US008686035B2

(12) United States Patent
Ueno et al.

(10) Patent No.: US 8,686,035 B2
(45) Date of Patent: *Apr. 1, 2014

(54) COMPOSITION AND METHOD FOR PROMOTING HAIR GROWTH

(75) Inventors: Ryuji Ueno, Montgomery, MD (US); Tsuyoshi Habe, Sasayama (JP); Takashi Sekida, Nishinomiya (JP)

(73) Assignee: R-Tech Ueno, Ltd., Tokyo (JP)

( * ) Notice: Subject to any disclaimer, the term of this patent is extended or adjusted under 35 U.S.C. 154(b) by 820 days.

This patent is subject to a terminal disclaimer.

(21) Appl. No.: 10/567,462

(22) PCT Filed: Aug. 12, 2004

(86) PCT No.: PCT/JP2004/011864
§ 371 (c)(1),
(2), (4) Date: Feb. 5, 2007

(87) PCT Pub. No.: WO2005/013928
PCT Pub. Date: Feb. 17, 2005

(65) Prior Publication Data
US 2008/0033036 A1 Feb. 7, 2008

Related U.S. Application Data

(60) Provisional application No. 60/494,121, filed on Aug. 12, 2003.

(51) Int. Cl.
*A01N 37/08* (2006.01)
*A61K 31/215* (2006.01)

(52) U.S. Cl.
USPC .......................................... 514/530; 514/880

(58) Field of Classification Search
USPC .................. 554/559; 514/559, 530, 880
See application file for complete search history.

(56) References Cited

U.S. PATENT DOCUMENTS

| | | | |
|---|---|---|---|
| 3,962,218 A | 6/1976 | Raduchel et al. |
| 4,088,775 A | 5/1978 | Skuballa et al. |
| 4,684,633 A | 8/1987 | Imagawa et al. |
| 5,001,153 A | 3/1991 | Ueno et al. |
| 5,073,569 A | 12/1991 | Ueno et al. |
| 5,106,869 A | 4/1992 | Ueno et al. |
| 5,137,915 A | 8/1992 | Ueno et al. |
| 5,166,174 A | 11/1992 | Ueno et al. |
| 5,166,175 A | 11/1992 | Ueno |
| 5,166,178 A | 11/1992 | Ueno et al. |
| 5,175,189 A | 12/1992 | Ueno |
| 5,208,256 A | 5/1993 | Ueno |
| 5,212,200 A | 5/1993 | Ueno et al. |
| 5,221,763 A | 6/1993 | Ueno et al. |
| 5,274,130 A | 12/1993 | Ueno et al. |
| 5,397,797 A | 3/1995 | Ueno |
| 5,432,174 A | 7/1995 | Ueno et al. |
| 5,523,461 A | 6/1996 | Ueno et al. |
| 5,534,547 A | 7/1996 | Ueno et al. |
| 5,547,968 A | 8/1996 | Ueno |
| 5,591,887 A | 1/1997 | Ueno et al. |
| 5,686,487 A | 11/1997 | Ueno |
| 5,905,091 A | 5/1999 | Fuller |
| 5,952,378 A | 9/1999 | Stjernschantz et al. |
| 6,225,348 B1 | 5/2001 | Paulsen |
| 6,235,781 B1 | 5/2001 | Weiner et al. |
| 6,242,485 B1 | 6/2001 | Ueno |
| 6,262,105 B1 | 7/2001 | Johnstone |
| 6,265,440 B1 | 7/2001 | Ueno et al. |
| 6,353,014 B1 | 3/2002 | Sallee et al. |
| 6,414,016 B1 | 7/2002 | Ueno |
| 6,452,039 B1 | 9/2002 | Ueno |
| 6,583,174 B1 | 6/2003 | Ueno et al. |
| 6,610,732 B2 | 8/2003 | Ueno |
| 7,351,404 B2 | 4/2008 | Woodward et al. |
| 7,388,029 B2 | 6/2008 | DeLong et al. |
| 7,407,987 B2 | 8/2008 | deLong et al. |
| 7,417,067 B2 | 8/2008 | Ueno et al. |
| 7,498,360 B2 | 3/2009 | Rask-Andersen et al. |
| 7,514,474 B1 | 4/2009 | Lipkin et al. |
| 7,517,912 B1 | 4/2009 | Lipkin et al. |
| 7,541,382 B2 | 6/2009 | Lipkin et al. |
| 7,550,508 B2 | 6/2009 | Lipkin et al. |
| 7,553,874 B2 | 6/2009 | Lipkin et al. |
| 7,553,875 B2 | 6/2009 | Lipkin et al. |
| 7,632,867 B2 | 12/2009 | Lipkin et al. |
| 7,632,868 B2 | 12/2009 | Lipkin et al. |
| 7,635,720 B2 | 12/2009 | Lipkin et al. |
| 7,638,557 B2 | 12/2009 | Lipkin et al. |
| 7,645,800 B2 | 1/2010 | Lipkin et al. |
| 7,649,021 B2 | 1/2010 | Lipkin et al. |

(Continued)

FOREIGN PATENT DOCUMENTS

CS 230650 B1 8/1984
EP 0 308 135 A 3/1989

(Continued)

OTHER PUBLICATIONS

W. Skuballa, B. Radüchel, O. Loge, W. Elger, and H. Vorbrüggen; 15,15-Ketals of Natural Prostaglandins and Prostaglandin Analogues. Synthesis and Biological Activities; Journal of Medicinal Chemistry, 1978, vol. 21, No. 5, pp. 443-447.
Hiroshi Suemune et al; Conversion of Limonene to Prostanoic Acid and 8-Isoprostanoic Acid, Chemical and Pharmaceutical Bulletin, vol. 34, No. 2, 1986, pp. 550-557, Pharmaceutical Society of Japan, Tokyo.
John Sih; Synthesis of Six-Membered-Ring Analogues of 6α-Carba-PGI₂, Journal of Organic Chemistry, vol. 47, No. 22, 1982, pp. 4311-4315, American Chemical Society, Washington, DC.
Skuballa et al., 15,15-Ketals of Natural Prostaglandins and Prostaglandin Analogues. Synthesis and Biological Activities; Journal of Medicinal Chemistry, 1978, vol. 21, No. 5, pp. 443-447.
Communication of a Notice of Opposition (with Notice and opposition attached) in corresponding European Patent Application No. 04771825.9-1211/1673058 dated Jul. 18, 2012.

(Continued)

*Primary Examiner* — Kendra D Carter
(74) *Attorney, Agent, or Firm* — Sughrue Mion, PLLC

(57) ABSTRACT

The present invention provides a method and composition for promoting hair growth in a mammal which comprises a prostaglandin compound having two hetero atoms at the 15 position as an active ingredient thereof.

11 Claims, No Drawings

(56) References Cited

U.S. PATENT DOCUMENTS

| | | |
|---|---|---|
| 2002/0037914 A1 | 3/2002 | Delong et al. |
| 2002/0044953 A1 | 4/2002 | Michelet et al. |
| 2002/0045659 A1 | 4/2002 | Michelet et al. |
| 2002/0052414 A1 | 5/2002 | Bernard et al. |
| 2002/0052416 A1 | 5/2002 | Michelet et al. |
| 2002/0172693 A1 | 11/2002 | DeLong et al. |
| 2003/0040528 A1 | 2/2003 | Ueno |
| 2003/0147823 A1 | 8/2003 | Woodward et al. |
| 2003/0165549 A1 | 9/2003 | Bernard et al. |
| 2003/0199590 A1 | 10/2003 | Cagle et al. |
| 2003/0216465 A1 | 11/2003 | Ueno |
| 2004/0115234 A1 | 6/2004 | Gewirtz |
| 2004/0235885 A1 | 11/2004 | Ueno et al. |
| 2005/0112075 A1 | 5/2005 | Hwang et al. |
| 2005/0123577 A1 | 6/2005 | Michelet et al. |
| 2005/0222195 A1 | 10/2005 | Ueno |
| 2005/0222232 A1 | 10/2005 | DeLong et al. |
| 2006/0121069 A1 | 6/2006 | DeLong et al. |
| 2007/0092466 A1 | 4/2007 | deLong et al. |
| 2007/0160562 A1 | 7/2007 | Brinkenhoff |
| 2007/0282006 A1 | 12/2007 | Woodward et al. |
| 2007/0286890 A1 | 12/2007 | Walt |
| 2007/0298134 A1 | 12/2007 | Iino et al. |
| 2008/0033036 A1 | 2/2008 | Ueno et al. |
| 2008/0070988 A1 | 3/2008 | Woodward et al. |
| 2008/0103184 A1 | 5/2008 | DeLong et al. |
| 2008/0241078 A1 | 10/2008 | DeLong et al. |
| 2008/0255227 A1 | 10/2008 | Ueno et al. |
| 2008/0269332 A1 | 10/2008 | Lin |
| 2008/0275118 A1 | 11/2008 | Shaw et al. |
| 2009/0018204 A1 | 1/2009 | Brinkenhoff |
| 2009/0088473 A1 | 4/2009 | Maxey |
| 2009/0111761 A1 | 4/2009 | Lipkin et al. |
| 2009/0111880 A1 | 4/2009 | Lipkin et al. |
| 2009/0111881 A1 | 4/2009 | Lipkin et al. |
| 2009/0111882 A1 | 4/2009 | Lipkin et al. |
| 2009/0111883 A1 | 4/2009 | Lipkin et al. |
| 2009/0111884 A1 | 4/2009 | Lipkin et al. |
| 2009/0111885 A1 | 4/2009 | Lipkin et al. |
| 2009/0111886 A1 | 4/2009 | Lipkin et al. |
| 2009/0111887 A1 | 4/2009 | Lipkin et al. |
| 2009/0111888 A1 | 4/2009 | Lipkin et al. |
| 2009/0111889 A1 | 4/2009 | Lipkin et al. |
| 2009/0111890 A1 | 4/2009 | Lipkin et al. |
| 2009/0111891 A1 | 4/2009 | Lipkin et al. |
| 2009/0234005 A1 | 9/2009 | Ishida et al. |
| 2009/0286769 A1 | 11/2009 | DeLong et al. |
| 2009/0298928 A1 | 12/2009 | Iino et al. |

FOREIGN PATENT DOCUMENTS

| | | |
|---|---|---|
| JP | 10-287532 A | 10/1998 |
| WO | 9511003 A1 | 4/1995 |
| WO | 03/030912 A1 | 4/2003 |
| WO | 2007023841 A1 | 3/2007 |
| WO | 2009035565 A1 | 3/2009 |
| WO | 2009140430 A1 | 11/2009 |

OTHER PUBLICATIONS

Prakash et al.; A Practical Route for the Synthesis of Prostaglandin $D_2$ Metabolites; Synthetic Communications, vol. 19, No. 1-2, p. 245-255 (1989).

Pis et al.; Preparation of 15,15-Acetals Analogues of Prostaglandin $F_{2A}$; Cesko-Slovenska Farmacie, vol. 39, No. 5, p. 205-209 (1990).

US 8,686,035 B2

COMPOSITION AND METHOD FOR PROMOTING HAIR GROWTH

CROSS REFERENCE TO RELATED APPLICATIONS

This is application is a National Stage of PCT/JP2004/011864 filed Aug. 12, 2004, which claims benefit of U.S. Provisional Application No. 60/494,121 filed Aug. 12, 2003.

TECHNICAL FIELD

The present invention relates to a composition and method for promoting hair growth in a mammalian subject.

BACKGROUND ART

Hair loss or alopecia may result from genetic factors, aging, local or systemic disease or certain therapeutic drugs designed to alleviate conditions such as cancer. Various preparations for preventing or reducing hair loss and/or promoting hair growth are proposed, for example those containing female hormones which can promote blood circulation, reinforce hair root function, moisturize scalp and inhibit male hormone function; 5α-reductase inhibitors; or minoxdil, trichosaccharides or the like as main ingredients. However, they cannot show satisfactory hair growth-promoting effects, and some may raise side-effect problems such as sexual function disorder.

It is strongly desired to develop a hair growth-promoting agent having superior effects without side effect.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

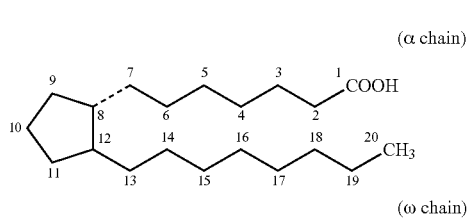

(A)
(α chain)
(ω chain)

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:
  Subscript 1: 13,14-unsaturated-15-OH
  Subscript 2: 5,6- and 13,14-diunsaturated-15-OH
  Subscript 3: 5,6-, 13,14-, and 17,18-triunsaturated-15-OH.
Further, the PGFs are classified, according to the configuration of the hydroxyl group at the 9- and 11-position, into α type (the hydroxyl group is of an α-configuration) and β type (the hydroxyl group is of β-configuration).

Certain prostaglandin compound having two hetero atoms at the 15 position are known in the art. U.S. Pat. No. 4,088,775 discloses certain 15-ethylenedioxy-prostanoic acid. In addition, U.S. Pat. No. 4,870,104 discloses 11 halo prostaglandins which may have an ethylenedioxymethylene group at 15-position and use thereof as agents inhibiting gastric acid secretion. Further, U.S. Pat. No. 6,353,014 discloses a certain 15-ketal analogs of F series prostaglandins useful for treating ocular hypertension and glaucoma.

Those prior arts do not disclose nor suggest that prostaglandin compound having two hetero atoms at the 15 position may be useful in the stimulation of hair growth.

DISCLOSURE OF THE INVENTION

An object of the present invention is to provide a composition for promoting hair growth in a mammalian subject.
Further object of the present invention is to provide a method for promoting hair growth in a mammalian subject.
Still further object of the present invention is to provide a novel compound useful for promoting hair growth in a mammalian subject.

Namely, the present invention relates to a composition for promoting hair growth in a mammalian subject which comprises a prostaglandin compound having two hetero atoms at the 15 position as an active ingredient thereof.

Further, the present invention relates to a method for promoting hair growth in a mammalian subject, which comprises topically administering a prostaglandin compound having two hetero atoms at the 15 position to the subject in need thereof.

Furthermore, the present invention relates to use of a prostaglandin compound having two hetero atoms at the 15 position for manufacturing a composition for promoting hair growth in a mammalian subject.

Still further, the present invention relates to a novel prostaglandin compound having two hetero atoms at the 15 position.

DETAILED DESCRIPTION OF THE INVENTION

The nomenclature of the PG compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds however, may also be named according to the IUPAC nomenclatures.

Examples of the analogs (including substituted derivatives) or derivatives include a PG compound of which carboxyl group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy lower) alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred prostaglandin compound used in the present invention is represented by formula (I):

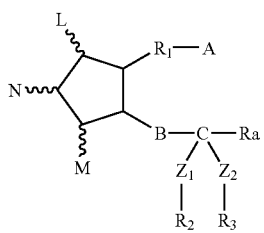

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH₃, or —CH₂OH, —COCH₂OH, —COOH or a functional derivative thereof;

B is —CH₂—CH₂—, —CH=CH— or —C≡C—;

Z₁ and Z₂ are oxygen, nitrogen or sulfur,

R₂ and R₃ are optionally substituted lower alkyl, which is optionally linked together to form lower alkylene, R₁ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

A more preferred prostaglandin compound used in the present invention is represented by the formula (II):

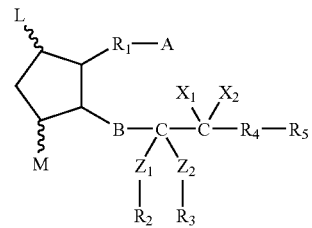

(II)

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH₃, or —CH₂OH, —COCH₂OH, —COOH or a functional derivative thereof;

B is —CH₂—CH₂—, —CH=CH— or —C≡C—;

Z₁ and Z₂ are oxygen, nitrogen or sulfur,

R₂ and R₃ are optionally substituted lower alkyl, which is optionally linked together to form lower alkylene, X₁ and X₂ are hydrogen, lower alkyl, or halogen;

R₁ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R₄ is a single bond or lower alkylene; and

R₅ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for R₁ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino) ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or arylsulfonylamides such as methylsulfonylamide, ethylsulfonylamide and tolylsulfonylamide.

Preferred examples of L and M include hydroxy and oxo, and especially, M and L are hydroxy groups which has a 5-membered ring structure of, so called, PGF type.

Preferred example of A is —COOH, its pharmaceutically acceptable salt, ester or amide thereof.

Preferred B is —CH$_2$—CH$_2$—, so called 13,14-dihydro type.

Preferred example of $X_1$ and $X_2$ is fluorine, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur.

Examples of $R_1$ include, for example, the following groups:

—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—O—CH$_2$—,
—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—, and
—CH$_2$—CH$_2$—CH$_2$—CH$_2$—CH$_2$—CH$_2$—CH(CH$_3$)—CH$_2$—.

Preferred Ra is a hydrocarbon containing 1-10 carbon atoms, more preferably, 1-8 carbon atoms. Ra may have one or two side chains having one carbon atom.

Preferred $Z_1$ and $Z_2$ are oxygen.

$R_2$ and $R_3$ are preferably linked together to form C2 or C3 alkylene.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, any of isomers such as the individual tautomeric isomers, the mixture thereof, or optical isomers, the mixture thereof, a racemic mixture, and other steric isomers may be used in the same purpose.

According to the present invention, a composition for promoting hair growth comprising the prostaglandin compound defined as above as an active ingredient is applied to a mammalian subject in need of promotion of hair growth.

The term "hair" in the present specification and claims covers any hair on a mammalian subject, especially a human subject, for example, hairs on the top of the head, on the armpits, on the pubic area, on the face including eyelash, eyebrow, eyelid, mustache, beard and whisker, on the chest, arms and legs.

The term "promoting hair growth" in the present specification and claims covers not only promoting hair growth but also promoting hair germination and thickening hairs. As is shown in the examples below, the composition of the present invention has the effect of thickening the growing hair in addition to the promotion of hair growth.

According to the present invention, the composition may be provided as, for example, pharmaceuticals, quasi-drugs (i.e. iyakubugaihin in Japanese) or cosmetics. The composition may topically be applied for the purpose of promoting hair growth onto the surface of skin where hair growth is desired, such as scalp, face, beard, head, pubic area, upper lip, eyelash, eyebrow, and eyelid.

The dose of the prostaglandin compound in the composition of the present invention may vary according to the compound to be used, the type of subject, age, skin area to be applied the composition, progress of baldness or desired effect, administration volume and period for treatment. Although a suitable concentration may be chosen as desired, in a typical case wherein the composition is topically administrated to an adult, the formulation containing 0.0000001%-10%, preferably 0.00001%-5%, more preferably 0.0001%-1% and especially 0.001-0.1% of the active ingredient can be applied 1-6 times, preferably 1-4 times per day.

The dosage form of the composition of the present invention can be any of known topically applicable forms. For example, but not limited thereto, lotion, tonic, emulsion, external drug creams such as liniments and milky lotions, external semi-solid preparations such as ointments, paste, jelly and sprays. The composition may also be formulated as hair shampoos or hair rinses.

The composition of the present invention may further contain physiologically acceptable additives. Said additives may include the ingredients used with the present compounds such as excipient, diluent, filler, resolvent, lubricant, adjuvant, binder, disintegrator, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. They may be further dissolved in an appropriate solvent such as fatty acid or its mono, di or triglyceride. The additives are well known to the art and may be selected from those described in general reference books of pharmaceutics or cosmetics.

The composition of the present invention may further contain other ingredients as far as they do not contradict the purpose of the present invention. The composition may be prepared in a conventional manner for manufacturing the desired formulations by adding the prostaglandin compound defined as above.

The further details of the present invention will follow with reference to test examples, which, however, are not intended to limit the present invention.

Synthesis Example 1

13,14-dihydro-15,15-trimethylenedioxy-20-ethyl-PGF$_{2\alpha}$ isopropyl ester (5)

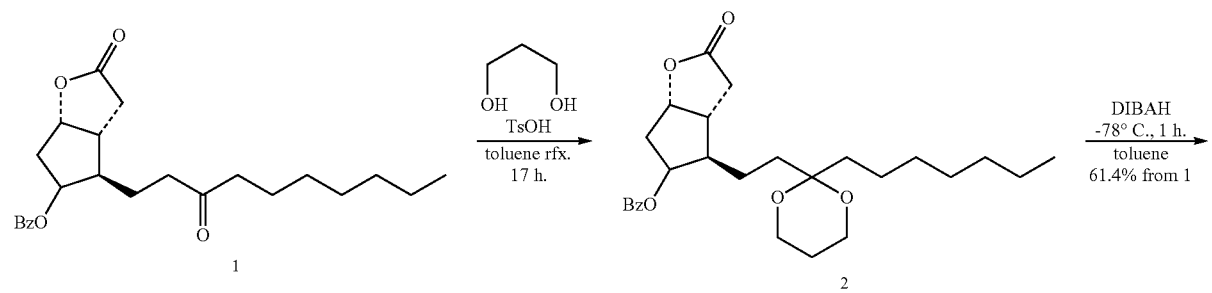

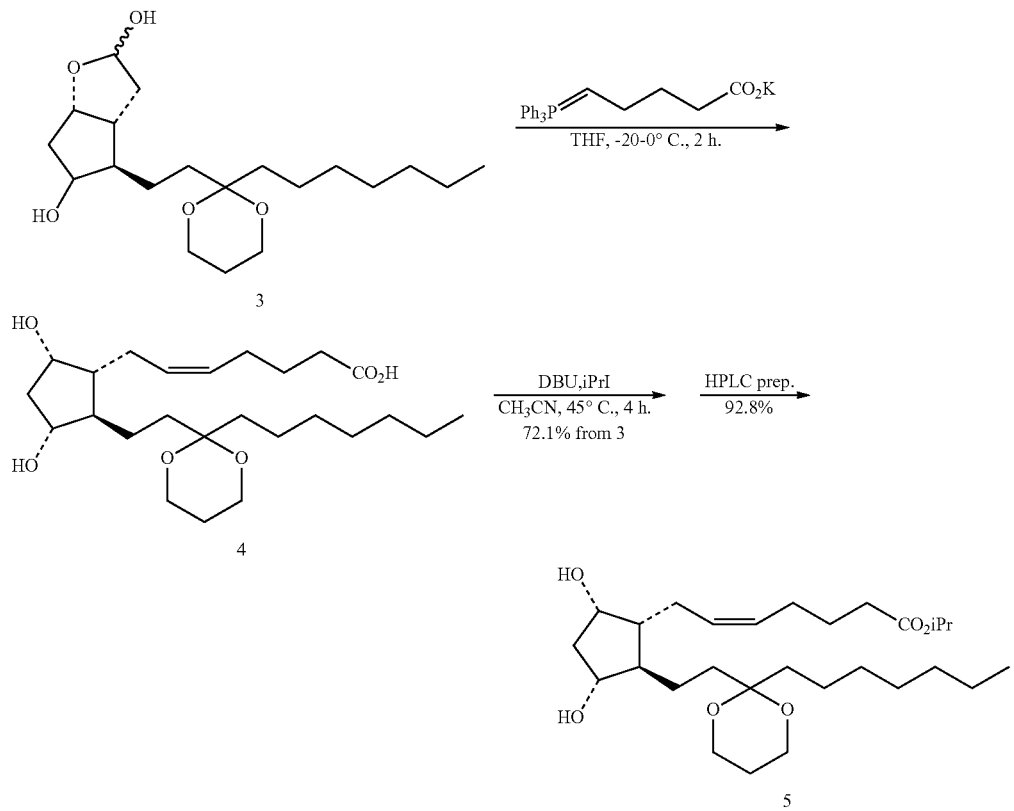

To the solution of compound 1 (510.0 mg, 1.273 mmol) in toluene (10.2 ml), 1,3-propanediol (0.92 ml, 12.73 mmol) and a catalytic amount of p-toluene sulfonic acid were added and the mixture was heated for 17 hours under reflux. After that, the reaction was left stood until it was cooled to room temperature, and washed with saturated aqueous sodium bicarbonate and saturated aqueous sodium chloride. The organic phase was dried with magnesium sulfate and evaporated under reduced pressure. The residue was purified by means of silica gel column chromatography (Merck 7734, Hexane: ethyl acetate=3:2) to give compound 2 (581.3 mg).

The solution of compound 2 (580.0 mg, 1.265 mmol) in toluene (11.6 ml) was cooled to −78° C., 1.5M-DIBAH (in toluene, 2.95 ml, 4.427 mmol) was added dropwise thereto and the mixture was stirred for 1 hour, and then, methanol (1.79 ml) was added dropwise to the resulting mixture. Saturated aqueous Rochelle salt (100 ml) was added thereto and the mixture was vigorously stirred for 30 minutes. The resulting mixture was extracted with ethyl acetate, and the organic layer was washed with saturated salt water, dried with magnesium sulfate and evaporated under reduced pressure. The residue was purified by means of silica gel column chromatography (Merck 7734, Hexane: ethyl acetate=1:9-0:10) to give compound 3 (275.2 mg, yield 61.4% from 1).

To the dispersion of (4-carboxybuthyl)triphenyl phosphonium bromide (1.346 g, 3.038 mmol) in THF (6 ml), 1M-potassium t-butoxide in THF (6.07 ml, 6.07 mmol) at 0° C. was added. The reaction was stirred for 1 hour at room temperature and then cooled to −20° C. Compound 3 (269.2 mg, 0.7594 mmol) in THF (7 ml) was added dropwise thereto and stirred for 2 hours at −20-0° C. Ice cold water was added to the reaction, THF was removed by evaporation evaporated under reduced pressure. To the concentrated residue at 0° C., ice cold 1N aqueous hydrochloric acid was added dropwise to adjust the solution to pH 4.

The solution was extracted with ethyl acetate and the organic layer was washed with saturated aqueous sodium chloride, dried with magnesium sulfate and evaporated under reduced pressure. The residue was added with ether and stirred for 17 hours at room temperature and then, filtrated with celite. The filtrate was evaporated under reduced pressure to give crude compound 4.

Compound 4 (0.7594 mmol) in acetonitrile (7.6 ml) was added with DBU (0.45 ml, 3.038 mmol), isopropyl iodide (0.30 ml, 3.038 mmol) and stirred for 4 hours at 45° C. The reaction mixture was evaporated under reduced pressure. The residue was added with water and extracted with ethyl acetate. The organic layer was washed with saturated aqueous sodium chloride solution, dried with magnesium sulfate and evaporated under reduced pressure. The residue was purified by means of silica gel column chromatography (Merck 9385, hexane:ethyl acetate=2:3) to give 727.2 mg of the desired product (yield 72.1% from 3). Thus obtained compound 4 (carboxylic acid, 259.0 mg) was further purified by separation HPLC to give compound 5 (isopropyl ester, 240.3 mg, HPLC purification yield 92.8%).

$^1$H-NMR spectrum (200 MHz, CDCl$_3$) of compound 5: δ5.57-5.14 (2H, m), 5.01 (1H, sept, J=6.2 Hz), 4.17 (1H, bs), 3.97 (1H, bs), 4.00-3.78 (4H, m), 2.76 (1H, d, J=6.2 Hz), 2.29

(2H, t, J=7.5 Hz), 2.44-2.06 (5H, m,), 1.88 (2H, bt,), 1.93-1.18 (22H, m), 1.23 (6H, d, J=6.2 Hz), 0.89 (3H, t, J=6.8 Hz)

Synthesis Example 2

13,14-dihydro-15,15-dimethoxy-20-ethyl-PGF$_{2\alpha}$ isopropyl ester (10)

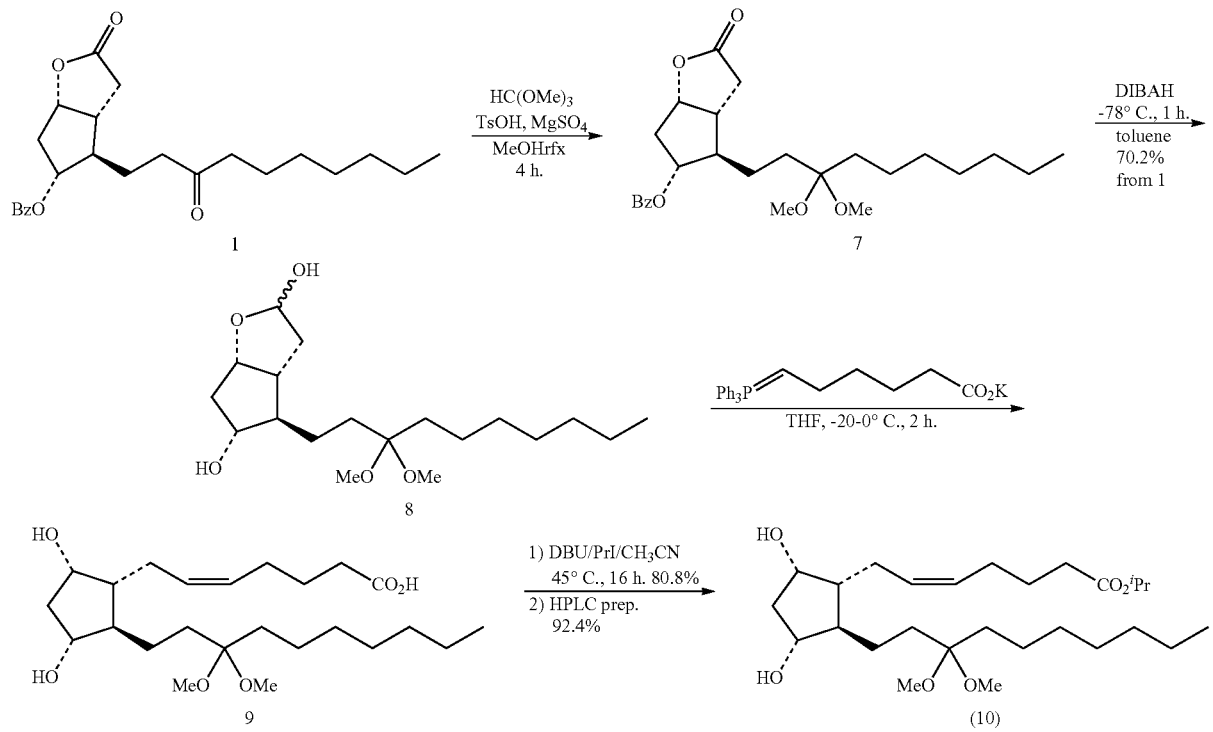

To the solution of compound 1 (797.8 mg, 2.002 mmol) in methanol (2.4 ml), a catalytic amount of p-toluene sulfate, methyl orthoformate (2.19 ml, 20.02 mmol) and unhydrous magnesium sulfate (1.20 g, 10.01 mmol) were added and heated under reflux for 4 hours. The reaction was cooled and added with sodium hydrogen carbonate, and filtered with celite. The filtrate was evaporated under reduced pressure and the residue was purified by means of silica gel column chromatography (Merck 7734 g, hexane:ethyl acetate=3:2) to give compound 7 (884.3 mg, yield 98.9%).

The solution of compound 7 (767.5 mg, 1.719 mmol) in toluene (15.4 ml) was cooled to −78° C., 1.5M-DIBAH (in toluene, 4.0 ml, 6.016 mmol) was added dropwise thereto and the mixture was stirred for 1 hour. Then, methanol was added dropwise to the reaction and the reaction was heated to room temperature. Saturated aqueous Rochelle salt (150 ml) was added thereto and the mixture was vigorously stirred for 30 minutes. The resulting mixture was extracted with ethyl acetate, and the organic layer was washed with saturated salt water, dried with magnesium sulfate and evaporated under reduced pressure. The residue was purified by means of silica gel column chromatography (Merck 9385, hexane: ethyl acetate=1:9) to give compound 8 (415.8 mg, yield 70.2%).

To the dispersion of (4-carboxybuthyl)triphenyl phosphonium bromide (1.250 g, 2.819 mmol) in THF, 1M-potassium t-butoxide in THF (5.64 ml, 5.64 mmol) at 0° C. was added. The reaction was stirred for 1 hour at room temperature and then cooled to −20° C. Compound 8 (242.8 mg, 0.7048 mmol) in THF (4 ml) was added dropwise thereto and stirred for 2 hours at −20-0° C. Ice cold water was added to the reaction, and THF was removed by evaporation under reduced pressure. To the residue at 0° C., ice cold 1N aqueous hydrochloric acid was added dropwise to adjust the solution to pH 5. The solution was extracted with ethyl acetate and the organic layer was washed with saturated aqueous sodium chloride, dried with magnesium sulfate and evaporated under reduced pressure. The residue was added with ether and stirred for 17 hours at room temperature and then, filtrated with celite. The filtrate was evaporated under reduced pressure to give crude compound 9 (carboxylic acid).

To the solution of compound 9 (0.7048 mmol) in acetonitrile (7 ml), DBU (0.42 ml, 2.819 mmol), isopropyl iodide (0.28 ml, 2.819 mmol) were added and the mixture was stirred for 16 hours at 45° C. The reaction mixture was evaporated under reduced pressure. The residue was added with water and extracted with ethyl acetate. The organic layer was washed with saturated aqueous sodium chloride, dried with magnesium sulfate and evaporated under reduced pressure. The residue was purified by means of silica gel column (Merck 9385, hexane:ethyl acetate=1:2) to give compound 10 (268.0 mg, yield 80.8% from 8).

Compound 10 obtained as above (total 370 mg) was further purified by separation HPLC to give purified compound 10 (341.9 mg, HPLC purification yield 92.4%).

$^1$H-NMR spectrum (200 MHz, CDCl$_3$) of compound 10: δ5.54-5.13 (2H, m), 5.00 (1H, sept, J=6.2 Hz), 4.18 (1H, bs), 3.95 (1H, bs), 3.16 (6H, s), 2.66 (1H, d, J=6.4 Hz), 2.29 (2H, t, J=7.3 Hz), 2.48-2.06 (5H, m), 1.89 (2H, bt), 1.79-1.17 (20H, m), 1.23 (6H, d, J=6.2 Hz), 0.89 (3H, t, J=6.8 Hz)

Synthesis Example 3

13,14-dihydro-15,15-ethylenedioxy-17-phenyl-18,19,20-trinor-PGF$_{2\alpha}$ isopropyl ester (12)

Compound 12 was prepared from compound 11 in a same manner as Synthesis example 1.

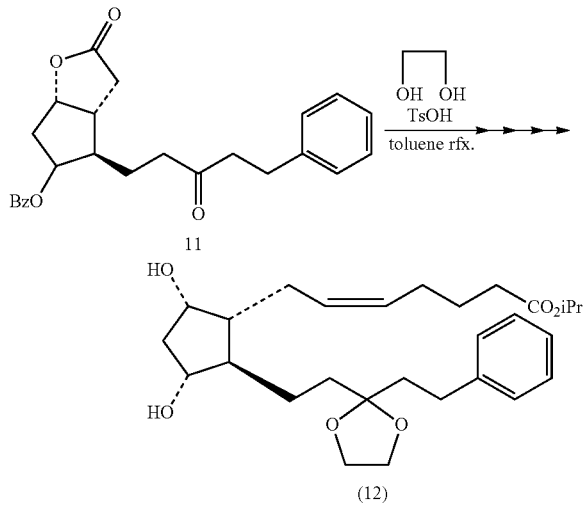

$^1$H-NMR spectrum (200 MHz, CDCl$_3$) of compound 11: δ8.04-7.93 (2H, m), 7.63-7.38 (3H, m), 7.35-7.11 (5H, m), 5.21-5.03 (2H, m), 2.98-2.24 (11H, m), 2.12-1.98 (1H, m), 1.80-1.50 (2H, m)

$^1$H-NMR spectrum (200 MHz, CDCl$_3$) of compound 12: δ7.35-7.12 (5H, m), 5.56-5.35 (2H, m), 5.00 (1H, sept, J=6.2 Hz), 4.15 (1H, bs), 3.96 (4H, s), 3.92 (1H, bs), 3.18 (1H, bd), 2.86 (1H, bd), 2.75-2.63 (2H, m), 2.28 (2H, t, J=7.3 Hz), 2.46-1.15 (17H, m), 1.22 (6H, d, J=6.2 Hz)

Synthesis Example 4

13,14-dihydro-15,15-ethylenedioxy-20-ethyl-PGF2α ethyl ester (15)

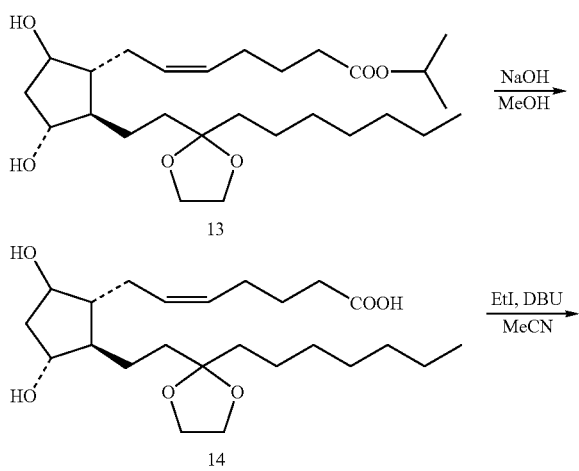

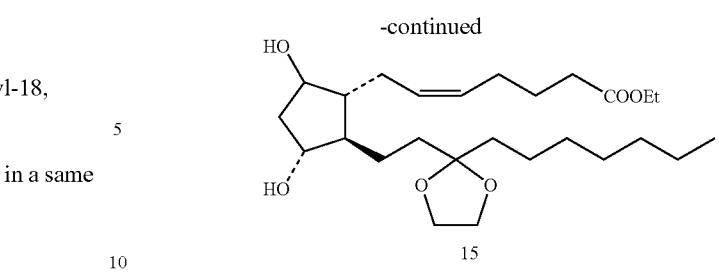

To the solution of compound 13 (9.18 g, 19.59 mmol) in methanol (91.8 ml), 8N-aqueous sodium hydroxide (24.49 ml) was added at 0° C. The reaction mixture was stirred for 3 hours at room temperature, and then acidified with 6N-hydrochloric acid at 0° C. The mixture was extracted with ethyl acetate (100 ml+50 ml). The organic layer was washed with saturated aqueous sodium chloride (100 ml×2), dried over anhydrous magnesium sulfate. The extract was evaporated under reduced pressure to obtain crude acid 14 as oil.

To the solution of crude acid 14 and 1,8-diazabicyclo[5.4.0]undec-7-ene (11.72 ml) in acetonitrile (60 ml), ethyl iodide (6.27 ml) was added dropwise at 0° C. The reaction mixture was stirred at 45° C. for 17 hours, then cooled to room temperature, and evaporated. To the residue, water (100 ml) was added. The mixture was extracted with ethyl acetate (100 ml×2). The organic layer was washed with 0.1N-hydrochloric acid, saturated aqueous sodium bicarbonate (100 ml) and saturated aqueous sodium chloride (100 ml). The extract was dried over anhydrous magnesium sulfate and evaporated. The residue was purified by two times of silica gel column chromatography (Merck 7734, 220 g, hexane:ethyl acetate=2:3,→BW-300, 210 g, hexane:2-Propanol=6:1) to obtain ethyl ester 15 (8.60 g, 18.92 mmol, 96.6% from 13) as a colorless oil.

$^1$H-NMR (200 MHz in CDCl$_3$, TMS=0 ppm) of the compound 15: δ5.58-5.29 (2H, m), 4.15 (1H, brs), 4.13 (2H, q, J=7.1 Hz), 3.97 (1H, brs), 3.94 (4H, s), 2.80-2.70 (1H, br), 2.49-2.36 (1H, m), 2.32 (2H, t, J=7.4 Hz), 2.36-2.15 (4H, m), 1.90-1.83 (2H, m), 1.83-1.12 (20H, m), 1.26 (3H, t, J=7.1 Hz), 0.88 (3H, t, J=6.5 Hz)

Example 1

Eight-weeks-old male C3H/HeN mice were used. The hair on the back was clipped by electric clipper so that the hair in the clipped area was removed as much as possible. Three days after the clipping, mice without visible scratches were selected and used in this study. Each group consisted of 3 animals. After group assignment, the groups were housed separately in aluminum cages (3 animals/cage, 180 mm W×300 mm D×130 mm H; Nippon Cage, Ltd., Japan).

Each test compound was dissolved in 70% (w/w) aqueous ethanol. Each dose formulation of test compound was evenly applied topically once daily (100 μL per mouse) to the clipped dorsal skin area (approximately 2×4 cm), except for Saturday and Sunday, for 30 days. The control group received an equal amount of the vehicle in the same manner.

Macroscopic observations of the hair growth were performed 14, 16, 18, 21, 23, 25, 28 and 30 days after the start of the treatment. Hair growth was scored according to the scale below:

− no hair growth observed
± hair growth≤10% of the clipped area
+ hair growth 10-40% of the clipped area
++ hair growth 40-80% of the clipped area
+++ hair growth ≥80% of the clipped area The results are shown in Table 1. In the vehicle-treated control group, no hair growth was observed during the treatment period. In the 0.01% and 0.1% compound A-treated groups, a dose-dependent hair growth was noted, and all animals treated with 0.1% compound A showed a hair growth classified to the highest score (+++) at Days 28 and 30 of treatment. In the 0.1% compound B-treated group, hair growth score for 2 out of 3 animals were +++ and that of the remaining animal was ++ at the end of the treatment period. In the 0.1% compound C-treated group, hair growth was observed on 1 out of 3 animals. In the 0.1% compound D-treated group, hair growth was observed on 2 out of 3 animals

TABLE 1

Effects of Topical Application of Compound A, B, C and D on Hair Growth in C3H/HeN Mice

| Groups | Animal No. | Hair Growth Score Days of Treatments | | | | | | | |
|---|---|---|---|---|---|---|---|---|---|
| | | 14 | 16 | 18 | 21 | 23 | 25 | 28 | 30 |
| Control (Vehicle) | 0101 | − | − | − | − | − | − | − | − |
| | 0102 | − | − | − | − | − | − | − | − |
| | 0103 | − | − | − | − | − | − | − | − |
| Compound A 0.1% | 0301 | − | ± | ± | + | ++ | +++ | +++ | +++ |
| | 0302 | − | − | ± | ± | ++ | ++ | +++ | +++ |
| | 0303 | − | ± | ± | ± | ++ | ++ | +++ | +++ |
| Compound A 0.01% | 0201 | − | − | − | − | − | − | ± | ± |
| | 0202 | − | − | − | − | − | + | + | + |
| | 0203 | − | − | ± | ± | ± | + | ++ | ++ |
| Compound B 0.1% | 0501 | − | − | ± | ± | + | ++ | ++ | ++ |
| | 0502 | − | − | − | ± | + | + | ++ | +++ |
| | 0503 | − | − | − | ± | + | ++ | ++ | +++ |
| Compound C 0.1% | 0701 | − | − | − | − | − | − | − | − |
| | 0702 | − | − | ± | ± | ± | + | + | + |
| | 0703 | − | − | − | − | − | − | − | − |
| Compound D 0.1% | 0901 | − | − | − | − | − | − | − | − |
| | 0902 | − | ± | ± | + | + | + | ++ | ++ |
| | 0903 | − | − | − | − | − | − | ± | ± |

Compound A: 13,14-dihydro-15,15-ethylenedioxy-20-ethyl-PGF$_{2\alpha}$ isopropyl ester
Compound B: 13,14-dihydro-15,15-ethylenedioxy-17-phenyl-18,19,20-trinor-PGF$_{2\alpha}$ isopropyl ester
Compound C: 13,14-dihydro-15,15-trimethylenedioxy-20-ethyl-PGF$_{2\alpha}$ isopropyl ester
Compound D: 13,14-dihydro-15,15-dimethoxy-20-ethyl-PGF$_{2\alpha}$ isopropyl ester Example 2

Eight-weeks-old male C3H/HeN mice were used. The hair on the back was clipped by electric clipper so that the hair in the clipped area was removed as much as possible. Three days after the clipping, mice without visible scratches were selected and used in this study. Each group consisted of 3 animals. After group assignment, the groups were housed separately in aluminum cages (3 animals/cage, 180 mm W×300 mm D×130 mm H; Nippon Cage, Ltd., Japan).

Test compound was dissolved in 75% aqueous ethanol. The formulation of test compound (compound E) was evenly applied topically once daily (100 µL per mouse) to the clipped dorsal skin area (approximately 2×4 cm), except for Saturday and Sunday, for 23 days. The control group received an equal amount of the vehicle in the same manner.

Macroscopic observations of the hair growth were performed 14, 16, 18, 21 and 23 days after the start of the treatment. Hair growth was scored according to the scale shown as above. Results are shown in Table 2. In the 0.1% compound E-treated group, hair growth was observed on 3 out of 3 animals.

TABLE 2

Effects of Topical Application of Compound E on Hair Growth in C3H/HeN Mice

| Groups | Animal No. | Hair Growth Score Days of Treatments | | | | |
|---|---|---|---|---|---|---|
| | | 14 | 16 | 18 | 21 | 23 |
| Control (Vehicle) | 0101 | − | − | − | − | − |
| | 0102 | − | − | − | − | − |
| | 0103 | − | − | − | − | − |
| Compound E 0.1% | 0201 | − | − | ± | ± | + |
| | 0202 | − | − | ± | ++ | ++ |
| | 0203 | − | − | − | + | ++ |

Compound E: 13,14-dihydro-15,15-ethylenedioxy-20-ethyl-PGF$_{2\alpha}$ ethyl ester Example 3

31 days after the start of the treatment conducted in Example 1, grown-up hairs in the treated area and hairs in the untreated area (i.e. non clipped area) were collected, respectively. Enlarged photomicrographs of the collected hairs were taken. Thickness of the randomly selected each ten hairs were measured and calculated the average.

Results are shown in Table 3. The results show that the hair grown-up by treating with the specific prostaglandin of the present invention was thicker than those in the untreated area.

TABLE 3

Effects of Topical Application of Compounds A and B on Thickness of Grown-up Hair in C3H/HeN Mice

| Hair group | n | Hair thickness, µm mean ± SE |
|---|---|---|
| Control area | 3 | 27.8 ± 2.6 |
| 0.1% Compound A-treated area | 3 | 34.1 ± 1.6 |
| Control area | 3 | 29.3 ± 1.0 |
| 0.1% Compound B-treated area | 3 | 33.3 ± 0.7 |

The invention claimed is:

1. A method for promoting hair growth in a mammalian subject, comprising administering a composition comprising an effective amount of a prostaglandin compound that is an ester of 13,14-dihydro-15,15-ethylenedioxy-20-ethyl-PGF$_{2\alpha}$ to the subject in need thereof.

2. The method as described in claim 1, wherein said prostaglandin compound is 13,14-dihydro-15,15-ethylenedioxy-20-ethyl-PGF$_{2\alpha}$ isopropyl ester.

3. The method as described in claim 1, wherein said prostaglandin compound is 13,14-dihydro-15,15-ethylenedioxy-20-ethyl-PGF$_{2\alpha}$ ethyl ester.

4. The method as described in claim 1, wherein the hair is selected from hair on top of head, hair on armpits, hair on pubic area, eyelash, eyebrow, hair on eyelid, mustache, beard, whisker, hair on chest, hair on arms and hair on legs.

5. The method as described in claim 1, wherein the hair is selected from hair on scalp, beard, hair on head, hair on pubic area, hair on upper lip, eyelash, eyebrow, and hair on eyelid.

6. The method as described in claim 1, wherein the hair is hair on scalp.

7. The method as described in claim 1, wherein the hair is eyelash.

8. The method as described in claim 1, wherein the prostaglandin compound of formula (I) is present in the composition in a concentration of 0.001-0.1%.

9. The method as described in claim 7, wherein the prostaglandin compound of formula (I) is present in the composition in a concentration of 0.001-0.1%.

10. The method as described in claim 7, wherein said prostaglandin compound is 13,14-dihydro-15,15-ethylenedioxy-20-ethyl-PGF$_{2\alpha}$ isopropyl ester.

11. The method as described in claim 7, wherein said prostaglandin compound is 13,14-dihydro-15,15-ethylenedioxy-20-ethyl-PGF$_{2\alpha}$ isopropyl ester, which is present in the composition in a concentration of 0.001-0.1%.

* * * * *

UNITED STATES PATENT AND TRADEMARK OFFICE
CERTIFICATE OF CORRECTION

PATENT NO.         : 8,686,035 B2
APPLICATION NO. : 10/567462
DATED              : April 1, 2014
INVENTOR(S)        : Ueno et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1341 days.

Signed and Sealed this
Thirtieth Day of May, 2017

Michelle K. Lee
*Director of the United States Patent and Trademark Office*